US005508386A

United States Patent [19]
Zanetti et al.

[11] Patent Number: 5,508,386
[45] Date of Patent: Apr. 16, 1996

[54] ANTIGENIZED ANTIBODIES AND GENES

[75] Inventors: Maurizio Zanetti; Maurizio Sollazzo, both of La Jolla, Calif.

[73] Assignee: The Regents of the University of California, Oakland, Calif.

[21] Appl. No.: 357,495

[22] Filed: Dec. 16, 1994

Related U.S. Application Data

[63] Continuation of Ser. No. 947,415, Sep. 18, 1992, abandoned, which is a continuation of Ser. No. 316,144, Feb. 24, 1989, abandoned.

[51] Int. Cl.$^6$ .......................... A61K 39/395; C07K 16/00; C07K 19/00

[52] U.S. Cl. .......................... 530/387.3; 530/387.1; 435/172.3; 435/69.6

[58] Field of Search .......................... 530/387.3, 387.1; 435/172.3, 69.6

[56] References Cited

PUBLICATIONS

Hird et. al. Genes and Cancer 1990, 184 John Wiley & Sons Ltd.
Waldmann Science vol. 252 :1657 1991.
Reichmann et al. Nature 332: 323, 1988.
Tao et. al. Journal Immunology 143: 2595 1989.
Lazar et. al. Molecular and Cellular Immunology 8: 1247 1988.
Burgess et al. Journal of Cell Biology 111: 2129 1990.

*Primary Examiner*—Lila Feisee
*Attorney, Agent, or Firm*—Walter H. Dreger

[57] ABSTRACT

Antibodies have been recombinantly produced which contain the NANP tetrapeptide of Plasmodium Falciparum within their third complementarity determining region in N-terminus of the variable region. These antibodies are capable of eliciting an antibody response.

3 Claims, 5 Drawing Sheets

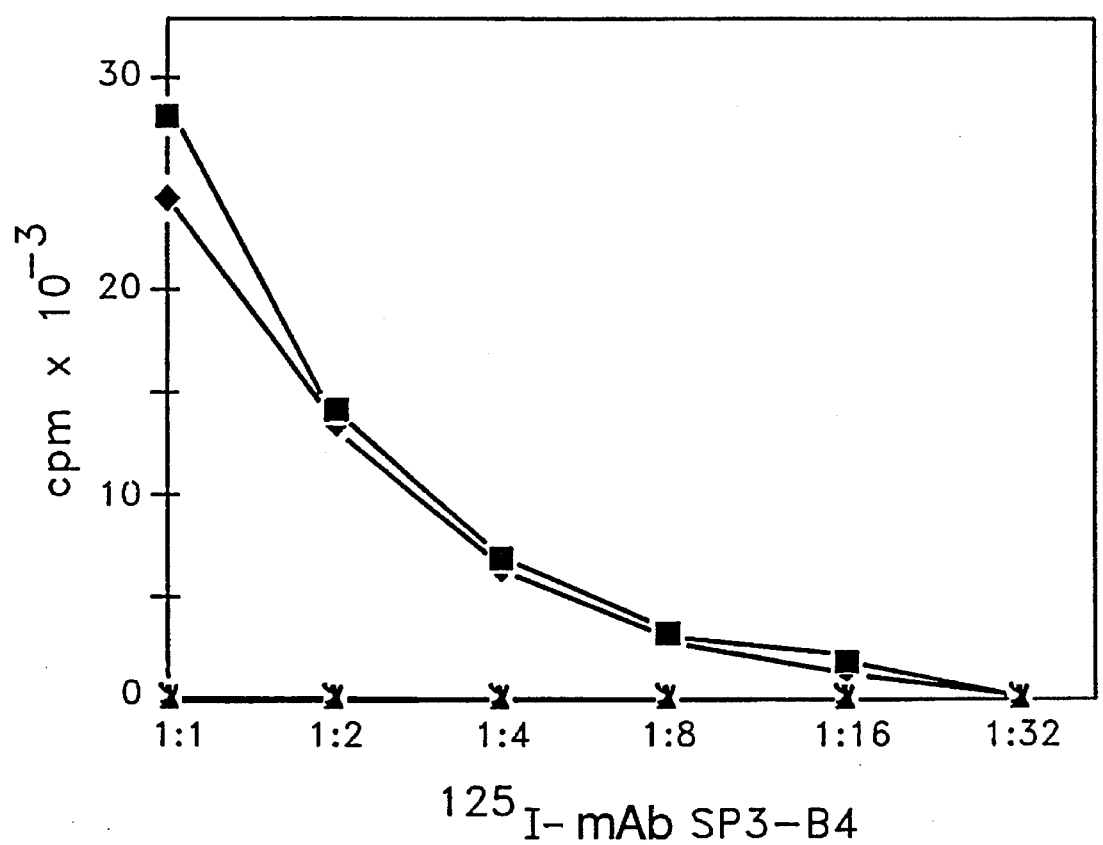

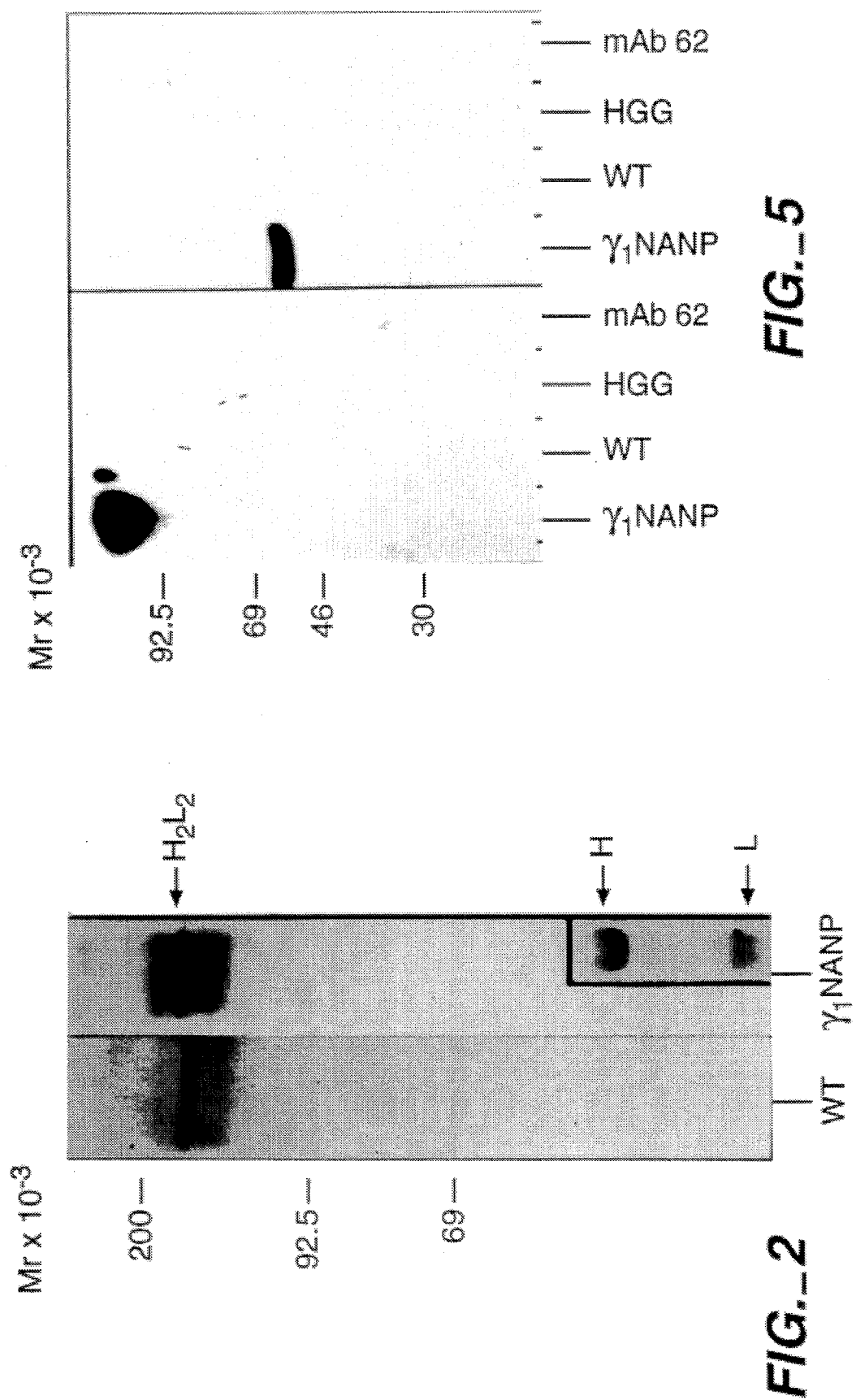
FIG._5
FIG._2

ANTIGENIZED ANTIBODIES AND GENES

This is a continuation of application Ser. No. 07/947,415 filed 18 Sep. 1992, now abandoned, which is a continuation of application Ser. No. 07/316,144 filed Feb. 24, 1989 now abandoned.

FIELD OF THE INVENTION

The present invention may utilize in its preferred embodiments, the use of recombinant DNA technology to genetically engineer natural or synthetically-derived immunoglobulin molecules, imparting therein novel epitopes, so as to create novel entities that can be employed in vitro and in vivo in a variety of means, such as to immunize against pathogens, and for example, build tolerance to antigens. In preferred embodiments, the epitopes are inserted into the so-called heavy or light chain variable domain of a given immunoglobulin molecule. Thus, known recombinant DNA technologies come to bear in the present invention, helping create novel immunoglobulin entities that retain functionality by localizing to particular cell types mechanistically via the so-called constant domains but otherwise functionally exploited to provide a novel localization of a particular antigenic determinant or epitope.

BACKGROUND OF THE INVENTION

Recombinant DNA technology has reached the point currently of being capable, in principle, of providing the methodology sufficient to identify, isolate and characterize DNA sequences, configure them for insertion into operative expression vectors and transfect those vectors variously into recombinant hosts such that those hosts are harnessed in their ability to produce the polypeptide encoded by the DNA sequence. Obviously, many variations attend the methodology associated with recombinant DNA technology, and particular means are not without inventive faculty. Nonetheless, methods are generally known in the published literature enabling requisite mental equipment for the art skilled to practice recombinant DNA technology in the production of polypeptides from a given recombinant host system.

Immunoglobulins (Igs) are the main effectors of humoral immunity, a property linked with their ability to bind antigens of various types. In view of the myriad numbers of antigens to a particular host organism, it can be appreciated that there are a like number or more of immunoglobulins that contain antigenic determinants or epitopes against particular such antigens. Immunoglobulin molecules are unique in their functionality of being capable of localizing to certain cell types, probably by means of mutual recognition of certain receptors that are located on the cell membrane. Immunoglobulins demonstrate a second general property whereby they act as endogenous modulators of the immune response. Igs and their idiotypic determinants have been used to immunize at the B- and/or T-cell level against a variety of exogenous antigens. In many cases, the immunity they evoke is comparable with that induced by the antigen itself. Although the principle underlying this phenomenon is understood, little is known about the molecular basis and the minimal structural requirements for the immunogenicity of Igs molecules and the interaction between those regions which may be responsible for such immunogenicity and the regions that are thought to provide the localization of a given immunoglobulin molecule with a particular cell/receptor type.

In the last many years, much progress has been made in endeavors to understand the immunogenic properties, structure and genetics of immunoglobulins. See Jeske, et al., *Fundamental Immunology,* Paul, ed., Raven Press, New York (1984), p 131 and Kabat, *Journal Immunology* 141, 525 (1988). Initially, the antigenicity of the so-called variable (V) domain of antibodies was demonstrated. Oudin, et al., *Academy of Sciences D* 257, 805 (1963) and Kunkel, et al., *Science* 140, 1218 (1963). Subsequently, further research pointed out the existence of discrete areas of variability within V regions and introduced the notion of hypervariable (HV) or complementarity-determining regions (CDR). Wu, et al., *J. Exp. Med.* 132, 211 (1970). Many studies since have indicated that the immunogenic property of Ig molecules is determined presumably primarily by amino acid sequence contained in the CDRs. Davie, et al., *Ann. Rev. Immunol.* 4, 147 (1986).

The basic immunoglobulin or antibody structural unit is well understood. The molecule consists of heavy and light chains held together covalently through disulfide bonds. The heavy chains are also covalently linked in a base portion via disulfide bonds and this portion is often referred to as the so-called constant region which is thought responsible for a given immunoglobulin molecule being mutually recognizable with certain sequences found at the surface of particular cells. There are five known major classes of constant regions which determine the class of the immunoglobulin molecule and are referred to as IgG, IgM, IgA, IgD and IgE. The N-terminal regions of the so-called heavy chains branch outwardly in a pictorial sense so as to give an overall Y-shaped structure. The light chains covalently bind to the Y branches of the two heavy chains. In the regions of the Y branches of the heavy chains lies a domain of approximately 100 amino acids in length which is variable, and therefore, specific for particular antigenic epitopes incidental to that particular immunoglobulin molecule.

It is to the Y branches containing the variable domains harboring the antigenic epitopes to which the particular attention is directed as a predicate of the present invention.

Prior researchers have studied and manipulated entire CDRs of immunoglobulins, producing chimeric molecules that have reported functionality. Exemplary attention is directed to Jones, et al., *Nature* 321, 522 (1986) reporting on a V-region mouse-human chimeric immunoglobulin molecule. This research thus amounted to a substantially entire CDR replacement as apparently does the research reported by Verhoeyen, et al., *Science* 239, 1534 (1988); Riechmann, et al., *Nature* 332, 323 (1988); and by Morrison, *Science* 229, 1202 (1985). See also European Patent Application Publication No. 125023A, published 14 Nov. 1984.

Bolstered by the successful research summarized above that resulted presumably in functional chimeric molecules, the goal of the present research was to explore further the variable region contained in the N-terminus Y branches. It was a goal of the present research to manipulate these variable regions by introduction or substitution of novel determinants or epitopes so as to create novel immunoglobulin molecules that would possibly retain the localization functionality and yet contain functional heterologous epitopes. In this manner, the novel immunoglobulin molecules hereof could be employed for use within the organism at foreign sites, thereby imparting immunity characteristics in a novel site-directed manner. A problem facing the present researchers at that time lay in the fact that epitopes are found in a region of the Y branch. Therefore, it was difficult to envision whether any manipulation of the variable region would be possible without disrupting the interaction of heavy chain with the corresponding light chain, and if that proved inconsequential, whether the resultant molecule would retain its functionality, with respect to the novel epitope, in combination with the constant region of the basic immunoglobulin molecule. Thus, even hurdling the problem of where to experiment, it was not possible to predict whether one could successfully produce such novel, bifunctional immunoglobulin molecules.

The present research and invention are based upon the successful threshold experiment, producing model, novel immunoglobulin molecules found to be fully functional by virtue of their ability to localize on certain cell/receptor sites and elicit reactivity to the antigens specific for the introduced novel antigenic determinant or epitope.

SUMMARY OF THE INVENTION

The present invention is based upon the successful production of novel immunoglobulin molecules having introduced into the N-terminus variable region thereof a novel epitope not ordinarily found in the immunoglobulin molecule used as a starting molecule.

The present invention is thus directed to novel immunoglobulin molecules having at least one novel heterologous epitope contained within the N-terminus variable domain thereof, said novel immunoglobulin molecule having retained functionality with respect to its C-terminus constant domain of the heavy chain specific for a particular cell/receptor type, and having novel, specific epitope in vitro and in vivo reactivity.

The present invention is further directed to pharmaceutical compositions containing, as essential pharmaceutical principle, a novel immunoglobulin hereof, particularly those in the form of an administrable pharmaceutical vaccine.

The present invention is further directed to methods useful for building tolerance to certain antigens, including those associated with autoimmune diseases, or for down-regulating hypersensitivity to allegens, or for providing active or passive immunity against certain pathogenic antigens, by administering to an individual in perceived need of such, a novel immunoglobulin molecule as defined above.

The present invention is further directed to novel recombinant means and methods useful for preparing, identifying and using the novel immunoglobulin molecules hereof including DNA isolates encoding them, vectors operatively harboring such DNA, hosts transfected with such vectors, cultures containing such growing hosts and the methods useful for preparing all of the above recombinant aspects.

DETAILED DESCRIPTION OF THE INVENTION

The present invention is described herein with particular detail for the preparation of model, novel immunoglobulin entities. This description is provided, as it was conducted, using recombinant DNA technology. Further detail herein defines methods by which one can test a given immunoglobulin to assure that it exhibits requisite functionality common to its starting material immunoglobulin and specially as to its novel epitopic antigenic activity. Given this information with respect to the particular novel immunoglobulin molecules described herein, coupled with general procedures and techniques known in the art, the art skilled will well enough know how to configure recombinant expression vectors for the preparation of other novel immunoglobulin molecules falling within the general scope hereof for use as herein described. Thus, having described the threshold experiment of the successful preparation of a novel immunoglobulin molecule, one skilled in the art need not follow the exact details used for reproducing the invention. Instead, the art skilled may borrow from the extant, relevant art, known techniques for the preparation of still other novel immunoglobulin molecules falling within the general scope hereof.

1. Figure Legends

FIG. 2 is an SDS-PAGE of the y1NANP and WT recombinant Ig.

FIG. 3 shows the binding of $^{125}$I-labelled monoclonal antibody Sp-3-B4 to engineered antibody y1NANP.

FIG. 5 shows results of cross-inhibition of $^{125}$I-labelled antibody Sp3-B4 binding to synthetic peptide (NANP)$_3$ (panel A) or engineered antibody y1NANP (panel B) by y1NANP Ig or peptide (NANP)$_3$.

2. General Methods and Definitions

Figure 1A:
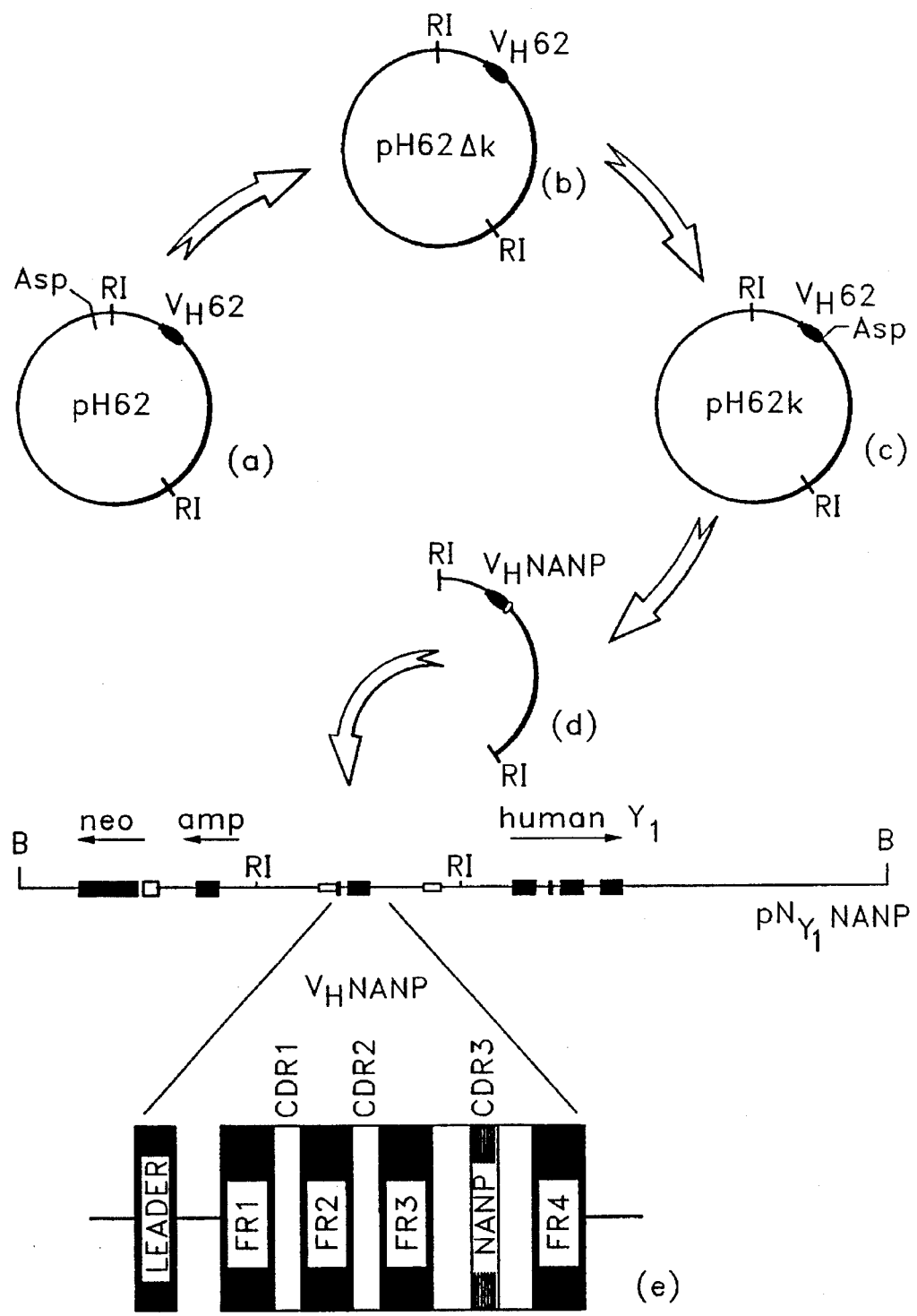
FIGS. 1A and 1B represent a diagram illustrating the construction of the pNy1NANP expression vector.

"Expression vector" includes vectors which are capable of expressing DNA sequences contained therein, where such sequences are operatively linked to other sequences capable of effecting their expression. It is implied, although not always explicitly stated, that these expression vectors may be replicable in the host organisms either as episomes or as an integral part of the chromosomal DNA. "Operative," or grammatical equivalents, means that the respective DNA sequences are operational, that is, work for their intended purposes. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" referred to as circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Apart from the novelty of the present invention involving the introduction of novel epitopes by means of repositioning or augmentation of a parent immunoglobulin, it will be understood that the novel immunoglobulins of the present invention may otherwise permissively differ from the parent in respect of a difference in one or more amino acids from the parent entity, insofar as such differences do not lead to a destruction in kind of the basic activity or bio-functionality of the novel entity.

"Recombinant host cells" refers to cells which have been transfected with vectors defined above.

Extrinsic support medium is used to support the host cells and includes those known or devised media that can support the cells in a growth phase or maintain them in a viable state such that they can perform their recombinantly harnessed function. See, for example, *ATCC Media Handbook*, Ed. Cote et al., American Type Culture Collection, Rockville, Md. (1984). A growth supporting medium for mammalian cells, for example, preferably contains a serum supplement such as fetal calf serum or other supplementing component commonly used to facilitate cell growth and division such as hydrolysates of animal meat or milk, tissue or organ extracts, macerated clots or their extracts, and so forth. Other suitable medium components include, for example, transferrin, insulin and various metals.

The vectors and methods disclosed herein are suitable for use in host cells over a wide range of prokaryotic and eukaryotic organisms.

"Heterologous" with reference herein to the novel epitope for a given immunoglobulin molecule refers to the presence of (at least one such epitope in the N-terminus domain of an immunoglobulin that does not ordinarily bear that epitope(s) in its native state. Hence, that chain contains heterologous epitope sequence(s). Such heterologous epitope sequences shall include the classic antigenic epitopes as well as receptor like binding domains or binding regions that s function as receptor sites, such as the human CD4 binding domain for HIV, hormonal receptor binding ligands, retinoid receptor binding ligands and ligands or receptors that mediate cell adhesion.

"Chimeric" refers to immunoglobulins hereof, bearing the heterologous epitope(s), that otherwise may be composed of parts taken from immunoglobulins of more than one species. Hence, a chimeric starting immunoglobulin hereof may have a hybrid heavy chain made up of parts taken from corresponding human and non-human immunoglobulins.

In addition to the above discussion and the various references to existing literature teachings, reference is made to standard textbooks of molecular biology that contain definitions and methods and means for carrying out basic techniques encompassed by the present invention. See, for example, Maniatis, et al, *Molecular Cloning: A Laboratory Manual*, Cold Spring Harbor Laboratory, N.Y., 1982 and the various references cited therein, and in particular, Colowick et al., *Methods in Enzymology Vol* 152, Academic Press, Inc. (1987). All of the herein cited publications are by this reference hereby expressly incorporated herein.

The foregoing description and following experimental details set forth the methodology employed initially by the present researchers in identifying and characterizing and preparing particular immunoglobulins. The art skilled will recognize that by supplying the present information including the wherewithal of the location and makeup of the epitope containing domain of a given immunoglobulin, and how it can be manipulated to produce the novel immunoglobulins hereof. Therefore, it may not be necessary to repeat these details in all respects in their endeavors to reproduce this work. Instead, they may choose to employ alternative, reliable and known methods, for example, they may synthesize the underlying DNA sequences encoding a particular novel immunoglobulin hereof for deployment within similar or other suitable, operative expression vectors and culture systems. Thus, in addition to supplying details actually employed, the present disclosure serves to enable reproduction of the specific immunoglobulins disclosed and others, and fragments thereof, such as the individual chains for in vitro assembly, using means within the skill of the art having benefit of the present disclosure. All of such means are included within the enablement and scope of the present invention.

3. Description of Particularly Preferred Embodiments

Protein engineering was used to introduce a foreign epitope into the CDR3 of the H chain of a mouse/human chimetic antibody ($C_{\gamma_1}62$). This epitope consists of three copies of the tetrapeptide Asn-Ala-Asn-Pro (NANP). The tetrapeptide occurs naturally as a 37 tandem repeat in the Plasmodium falciparum circumsporozoite (CS) protein, interspersed with four repeats of the variant sequence Asn-Val-Asp-Pro [Dame et al., *Science* 225, 593 (1984)]. In the construct described here, the epitope is flanked by Val and Pro residues at each end [VP (NANP)$_3$ VP]. The experiment verified that the (NANP)$_3$ epitope could be inserted in the HV region of a host H chain ($V_H$) without altering the framework folding of the Ig molecule, i.e., its molecular assembly with the light (L) chain and it determined that the antigenic and immunogenic properties of the recombinant Ig molecule were expressed. It is known that the CDR3 of $V_H$ regions of antibody is often the structural correlate of an immunodominant idiotope [Davie, et al, *Ann. Rev. Immunol*, 4, 147 (1986)], which indicates that the CDR3 is at the surface of the molecule. Moreover, it is well established that because of recombination of the variable-diversity-joining (VDJ) regions, as well as N-addition mechanisms [Tonegawa, *Nature* 302, 575 (1983); Miller et al., *Immunol. Today* 7, 36 (1986)], the CDR3 may vary considerably in length (from 3 to 19 amino acids) [Kabat, et al., *Proteins of Immunological Interest*, U.S. Dept. of Health and Human Service NIH (1987)], implying a high degree of plasticity at the structural level. Second, the (NANP)$_3$ epitope selected for this study is relatively short, repetitive and of proven immunogenicity in mice and humans [Good et al., *Ann. Rev. Immunol*. 6, 663 (1988)].

4. Examples

The production of hybridoma 62 and B1OH2, and the purification of mAb 62 and 109.3 (anti-2,4-dinitrophenol) have been described previously [Zanetti et al., *J. Immunol*. 131, 2452 (1983) and Glotz et al., *J. Immunol*. 137, 223 (1986)].

A DNA library was constructed from size-selected 2-2.5-kb Eco RI fragments from hybridoma 62 genomic DNA. Fragments were eluted from low melting point agarose and ligated into the λgt10 vector [Huynh et al., *DNA Cloning Techniques* 1, 49 (1985)]. After ligation and packaging, $5 \times 10^4$ plaque-forming units were screened by replicate hybridization with the $J_H$ [Sakano et al., *Nature* 286, 676 (1980)] and pSAPC15 [Brodeur et al., *Eur. J. Immunol*. 14, 922 (1984)] probes. Four clones were isolated and plaque purified; the 2.3-kb EcoRI insert form one of them was subcloned into pEMBL18 vector [Dente et al., *DNA Cloning Techniques* 1, 101 (1985)]. The $V_H$B10H2 coding sequence was determined by cloning the cDNA from the parental hybridoma by primer extension of the poly(A)$^+$ RNA with a synthetic oligonucleotide (5'GGGGCCAGTGGATAGAC3') that anneals at the 5' end of the CH1 region. The same oligonucleotide was used as a probe for screening the library after 5' end-labeling by kinase with $^{32}$P-ATP. The nucleotide sequence of both clones was determined by dideoxy method on both strands after subcloning suitable restriction fragments into the pEMBL18 vector.

Plasmid $pN_{\gamma1}62$ containing DNA encoding $C_1,62$ antibody was constructed by subcloning in the proper orientation the 2.3-kb EcoRI DNA fragment carrying the $V_H62$ rearrangement into the unique EcoRI site of the $PN_{\gamma1}$ vector [Sollazo et al., *Focus* 50, 64(1988)] (a PSV derived vector harboring an human $\gamma_1$, gene). This vector encodes a human $\gamma_1$ gene downstream from the EcoRI site. It also carries a neomycin resistance gene under the control of the SV40 promoter for the selection of stable transformant cells. Transfectoma cells were constructed by introducing the plasmids $pN_{\gamma1}62$ and $pN_{\gamma1}$CHA, a chimeric construct encoding an antibody lacking Id62 and Ig binding into J558L mouse by electroporation. This cell line is an H chain-defective variant of myeloma J558 [Morrison et al., *Science* 229, 229 (1985)] and carries the rearrangement for a λ1 light (L) chain. Briefly 3× $10^6$ cells in 1 ml of Dulbecco's modified minimum essential medium (DMEM) containing 10 μg of supercoiled plasmid DNA were pulsed for 17 ms at 650 V/cm in a Cell Porator apparatus (Bethesda Research Laboratories, Bethesda, Md.). After pulsing, the cells were resuspended in 10 ml of DMEM supplemented with 10 mM Hepes buffer, 2 mM L-glutamine, penicillin (50 μg/ml), streptomycin (50 μg/ml) and 10% fetal calf serum (cDMEM), and incubated for 48 h at 37° C. in a 10% $CO_2$ atmosphere. The cells were then resuspended in 20 ml of cDMEM and an aliquot (2 ml) was diluted into 20 ml of cDMEM containing 1.2 mg/ml of G418 (Gibco, Grand Island, N.Y.), plated on a 96-well microtiter plate and cultured for 14 days. The supernatants of neomycin-resistant colonies (stable transformants) were tested by solid-phase radioimmunoassay (RIA) and enzyme-linked immunosorbent assay (ELISA).

The presence of Id62 in the supernatant of J558L cells transfected with $pN_{65\ 1}62$ vector was tested by competitive inhibition in ELISA. This measures the inhibition (percent) of the binding of horseradish peroxidase (HP)-conjugated mAb 62 (ligand) to anti-Id62 antibody coated on 96-well polyvinyl microtiter plate (Dynatech, Alexandria, VA) [Zanetti et al., *J. Immunol.* 131, 2452 (1983)]. The supernatant of J558L cells transfected with $pN_{\gamma 1}$CHA plasmid and purified mAb 62 and 109.3 (an $IgG_1$, x anti-2,4-dinitrophenol) served as controls [Zanetti et. al., *J. Immunol.* 131, 2452 (1983)]. A second method to test for Id62 expression was by Western blot [Towbin et al., *Proc. Natl. Acad. Sci. USA* 71, 4350 (1979)]. Briefly, approximately 5 μg of antibody $c_{\gamma 1}62$ purified by affinity chromatography on an anti human Ig Sepharose 4B column (Pharmacia, Uppsala, Sweden) was electrophoresed on a 10% sodium dodecyl sulfate polyacrylamide gel electrophoresed on a 10% sodium dodecyl sulfate polyacrylamide gel electrophoresis under reducing conditions. The gel was then blotted onto 0.45M nitrocellulose paper (Millipore, Bedford, Mass.) and probed with $^{125}$I-labelled affinity-purified syngeneic anti-Id62 antibody [Zanetti et al. *J. Immunol.* 135, 1245 (1985)]. Antibodies 62 and 109.3 served as positive and negative control, respectively. The filter was exposed a first time for 24 h at –70° C. with intensifier screen. To demonstrate the co-expression of the human C region on the H chain of the chimeric $c_{\gamma 1}62$ antibody, the nitrocellulose paper was re-probed with $^{125}$I-labelled goat anti-human Ig antibody and exposed for 2 h at 70° C.

Sequence data is publicly available from EMBL/Gene Bank Data Library under Accession No. Y00744.

Figure 1B:
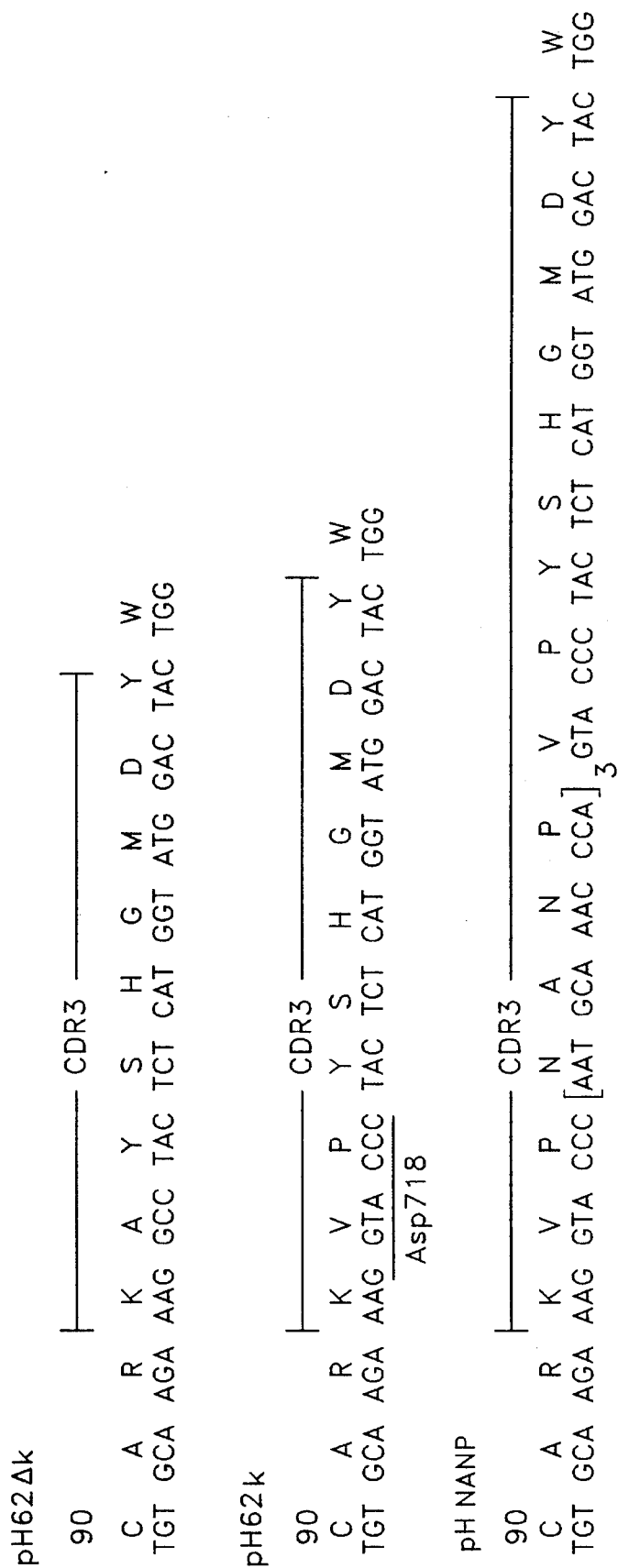

The $y_1$NANP antibody carrying the malarial CS immunodominant B-cell epitope NANP in the CDR3 of its H chain was engineered as follows:

FIG. 1 is a diagram illustrating the construction of the pNy1NANP expression vector. In panel A: (a) The productively rearranged $V_H$ gene of the hybridoma cell line 62 isolated from a size-selected lambda gt10 library and subcloned into p-Bluescript (publicly available from Stratagene, San Diego, Calif.) is described infra.; (b) The restriction site Kpn I/Asp718 of the polylinker region was deleted by Kpn I digestion, filled in with T4 polymerase and ligated, yielding the plasmid pH62Δk; (c) pH62Δk was used as a template for site-directed mutagenesis to introduce a unique Asp718 restriction site in CDR3 of the $V_H$ gene. The synthetic oligonucleotide (5'CAAGAAAGGTACCCTACTCTC 3'), which encodes a 3 bp insertion (TAC), was annealed to the uracylated single-stranded complementary template and elongated; (d) Complementary synthetic oligonucleotides (5'GTACCCAATGCAAACCCAAATGCAAAC-CCAAATGCAAACCCA 3' 3'GGTTACGTTTGGGTT-TACGTTTGGGTTTACGTTTGGGTCATG 5')

were annealed and subcloned into the unique Asp718 site of pH62k. The construction was verified by sequence analysis by using a $15^{mer}$ primer corresponding to the 5' end of $V_H62$ gene (5'GACGTGAAGCTGGTG 3'); (e) The 2.3-kb Eco RI fragment carrying the engineered $V_H$NANP gene was subcloned upstream from the human yl C region into the 15-kb pNyl vector. The pNy1NANP construct was electroporated into J558L cells subsequently cultured in the presence of G418. Resistant clones were screened for Ig production by a sandwich enzyme-linked immunosorbent assay (ELISA) using goat anti-human antibodies immobilized on microtiter wells as the capturing antibodies and horseradish peroxidase (HP) conjugated goat anti-human Ig (Sigma) as the revealing antibodies. Clones producing >2–5 μg Ig/ml of protein $10^6$ cells were expanded and the antibody purified from culture supernatants. Sequence modifications illustrated in panel A are shown in detail in panel B. Abbreviations used: Asp—Asp 718; B—Bam HI; RI—Eco RI; FR—framework region; CDR—complementarily-determining region; neo—neomycin (G418) resistance; amp—ampicillin resistance.

The restriction fragment encoding the $V_H$ gene of a murine monoclonal antibody to thyroglobulin (mAb 62) was modified as shown in FIG. 1. A double-stranded synthetic DNA fragment encoding three copies of the NANP tetramer (NANP)$_3$ and carrying Asp718 protruding ends was inserted in frame between Pro 95 and Tyr 96 of $V_H$62k coding region. The pH62NANP construct was verified by dideoxy sequencing. The Eco RI restriction fragment encoding the engineered $V_H$ was subcloned into the $pNY_1$ expression vector upstream from the human $Y_1$ constant (C) region to obtain the $pNY_1$NANP construct. This plasmid was electroporated into the murine J558L cell line, a H chain-defective variant of myeloma J558 that carries the rearrangement for a lambda-1 L chain [Morrison et al., *Science* 229, 1202 (1985)].

Transfectoma cells were cultured, subcloned and screened for secretion of the engineered Ig molecule using a sandwich enzyme-linked immunosorbent assay (ELISA) with goat anti-human Ig antibodies. Clones producing 2–5 μg/ml of protein $10^6$ cells were selected and expanded, and the chimeric protein was purified by means of affinity chromatography on a Sepharose 4B-Protein-A column. The purified Ig molecule was analyzed by SDS-PAGE under reducing and nonreducing conditions.

FIG. 2 is an SDS-PAGE of the y1NANP and WT recombinant Ig. Five μg of Protein A-purified antibody were loaded on a 7.5% polyacrylamide gel under nonreducing conditions. The gel was stained with Comassie blue. The inset shows the resolution into heavy (H) and light (L) chains of engineered antibody y1NANP electrophoresed on a 10% polyacrylamide gel under reducing (5% β-mercaptoethanol) conditions.

FIG. 2 shows that the nonreduced $y_1$NANP chimeric antibody has an apparent molecular weight of 160 kD, suggesting a proper $H_2L_2$ assembly to form a tetrameric Ig protein. When the $y_1$NANP antibody was compared with the wild-type (WT) Ig, a chimeric antibody lacking the (NANP)$_3$ insert, purified from culture supernatant fluid of J558L cells transfected with $pNy_{162}$, a slight difference in size was observed due to the presence of the inserted epitope. However, the molecular weight of the $y_1$NANP antibody is well in the range of a tetrameric complex. Both preparations also showed a smear in the region below the 160 kD band, suggesting some degradation and/or noncorrectly assembled protein products. Under reducing conditions, the engineered $y_1$NANP antibody was appropriately resolved into an H and na L chain (FIG. 2, inset). As determined by ELISA of NP-40 lysates, transfectoma cells secreting the $y_1$NANP antibody had approximately the same cytoplasmic levels of H chains as cells producing the WT Ig. Collectively, these results indicate that the insertion of 15 amino acids into the CDR3 of $V_H 62$ did not appreciably alter the interaction between $V_H$ and $V_L$ polypeptide chains nor the assembly and secretion of the tetrameric ($H_2L_2$) Ig molecule.

To determine if the engineering $y_1$NANP antibody indeed expresses the (NANP)$_3$ epitope in an immunological accessible form, solid-phase radioimmunoassay (RIA) and Western blot techniques were used and a murine monoclonal antibody (Sp3-B4) generated against *P. falciparum* and specific the NANP epitope.

FIG. 3 shows the binding of $^{125}$I-labelled monoclonal antibody Sp-3-B4 to engineered antibody y1NANP. Murine monoclonal antibody (mAb) Sp3-B4, an IgG2a,k antibody produced by immunization with the *P. falciparum* parasite and reacting with the repetitive epitope NANP. Specific for the NANP epitope, any antimalarial antibody could be so used as a tool and generated via analogous techniques. Polyvinyl microtiter wells were coated by drying at 37° C. with 5 µg/ml solution in 0.9% NaCl of purified y1NANP Ig (solid diamonds), WT (solid triangles), (NANP)$_3$ synthetic peptide (solid squares), a $16^{mer}$ synthetic peptide (YYCARKAYSHGMDYW) encompassing the CDR3 of the $V_H$ region of prototype antibody 62 (open squares), and the $15^{mer}$ synthetic peptide YPQVTRGDVFTMPED of the cell-adhesive molecule vitronectin (open diamonds). The $^{125}$I-labelled antibody Sp3-B4 (20×10$^4$ cpm/50 µl) was incubated overnight at +4° C. After extensive washing, the bound radioactivity was counted in a gamma counter. The test was done in triplicate.

The results of the direct RIA binding (FIG. 3) showed that $^{125}$I-labelled mAb Sp3-B4 bound both the synthetic peptide (NANP)$_3$ and the recombinant $y_1$NANP antibody immobilized on microtiter wells. However, the binding to antibody $y_1$NANP can be considered more efficient; in molar terms, the estimated ratio of peptide to antibody was about 50 to 1, assuming that the antibody expresses two copies of the (NANP)$_3$ epitope per Ig molecule. No binding occurred to either the WT Ig or two irrelevant synthetic peptides, one corresponding to the CDR3 sequence of prototype $V_H 62$ and the other to residues YPQVTRGDVFTMPED of vitronectin.

Figure 4A:
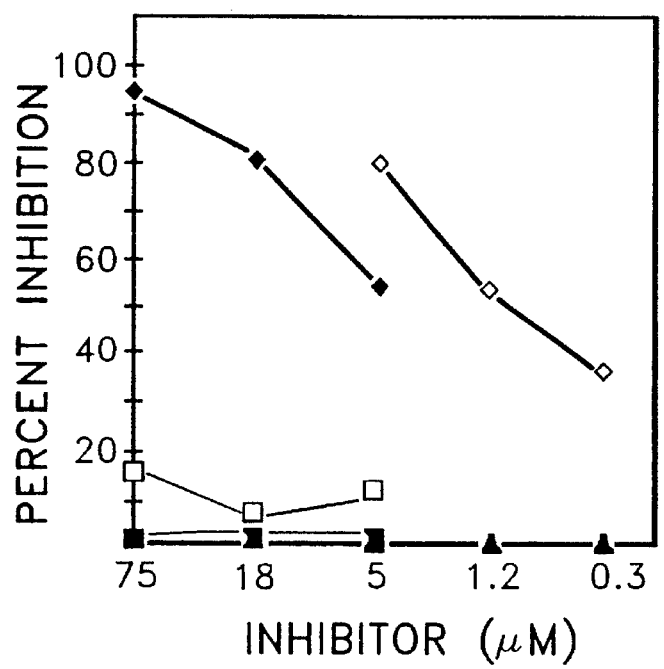
FIGS. 4A and 4B represent a Western blot binding of $^{125}$I-labelled antibody Sp3-B4 to engineered antibody y1NANP and localization of the engineered (NANP)$_3$ epitope in the H chain.
Figure 4B:
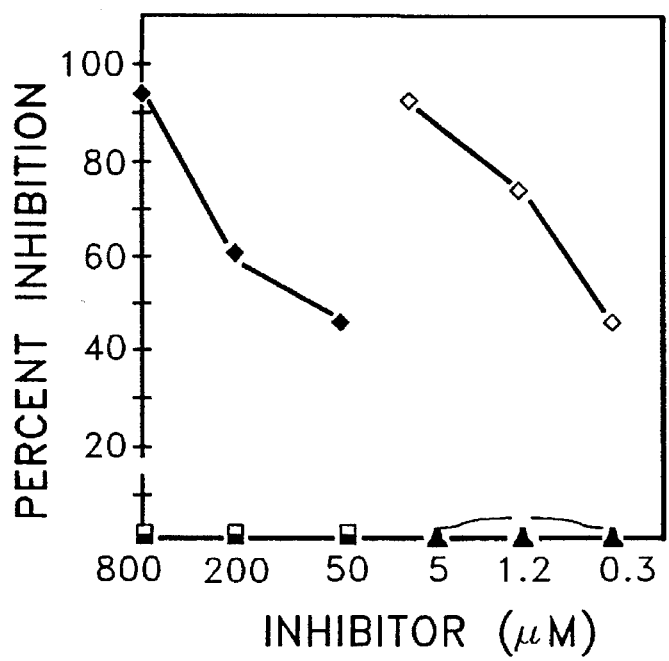

FIG. 4 is a Western blot binding of $^{125}$I-labelled antibody Sp3-B4 to engineered (NANP)$_3$ epitope in the H chain. Ten µg of purified y1NANP Ig, recombinant WT Ig, native monoclonal antibody 62, and polyclonal human gamma globulins (HGG) (Cohn fraction II, Miles) were loaded onto a 10% SDS-PAGE and electrophoresed at 150 V under nonreducing (left panel) and reducing (right panel) conditions. Resolved proteins or polypeptide chains were transferred from the gel to 0.45-µm nitrocellulose paper. After blotting, the filter was blocked with 10% solution of dry milk in 0.9% NaCl for two hours at room temperature. The sheet was then incubated overnight at +4° C. by rocking with $^{125}$I-labelled antibody Sp3-B4 (40×10$^4$ cpm/ml) in phosphate-buffered saline, pH 7.3, containing 1% bovine serum albumin and 1% Tween 20. After incubation, the filter was washed extensively, dried and exposed to Kodak XAR-5 film at −70° C. for 18 hours. Binding to y1NANP Ig, recombinant WT Ig, antibody 62 and HGG in RIA by the same $^{125}$I-labelled probe (10$^5$ cpm/50 µl) was 10,560; 420; 360; and 330 cpm, respectively.

Western blot analysis (FIG. 4) showed that $^{125}$I-labelled mAb Sp3-B4 specifically bound antibody $y_1$NANP in both the nonreduced (left panel) and reduced (right panel) forms. In the latter, as expected, binding occurred on the H- but not the L-chain, confirming that the engineered $y_1$NANP antibody bears the (NANP)$_3$ epitope on the H chain. No binding occurred to controls for the H and L chain and the human C region.

A cross-inhibition assay was employed to assess the engineered $y_1$NANP antibody's relative efficiency in expressing the (NANP)$_3$ epitope. The synthetic peptide (NANP)$_3$ and antibody $y_1$NANP were used to inhibit the binding of $^{125}$I-labelled mAb Sp3-B4 to either the (NANP)$_3$ peptide or the $y_1$NANP antibody immobilized on microtiter plates.

FIG. 5 shows results of cross-inhibition of $^{125}$I-labelled antibody Sp3-B4 binding to synthetic peptide (NANP)$_3$ (panel A) or engineered antibody y1NANP (panel B) by y1NANP Ig or peptide (NANP)$_3$. A fixed amount of $^{125}$I-labelled antibody Sp3-B4 (probe) was mixed vol/vol with decreasing amounts of the various inhibitors diluted in phosphate-buffered saline, pH 7.3, containing 1% bovine serum albumin and 1% Tween 20. The mixture was incubated at +4° C. overnight by rocking. Fifty µl of each mixture were incubated on individual polyvinyl microtiter wells coated with either synthetic peptide (NANP)$_3$ (panel A) or purified engineered y1NANP Ig (panel B). The conditions of coating are as detailed in the legend to FIG. 4. The following inhibitors were used: purified y1NANP Ig, WT Ig, and synthetic peptides (NANP)$_3$, CDR3 and vitronectin. The percentage of inhibition was calculated as follows: [(average binding of the probe alone)—(average binding of the probe incubated in the presence of inhibitor)]/(average binding of the probe alone)× 100. Tests were done in duplicate.

FIG. 5 shows that both the peptide and the engineered antibody efficiently inhibited the binding to both physical forms of the (NANP)$_3$epitope, i.e., synthetic peptide and antibody borne. However, whereas the $y_1$NANP antibody was about four times more effective than the peptide itself (panel A) in inhibiting binding to the synthetic peptide, it was approximately 150 times more effective than the peptide in inhibiting binding to the engineered Ig (panel B). The WT Ig and control peptides (CDR3 and vitronectin) caused no inhibition. Thus, when compared with the synthetic peptide it appears that the (NANP)$_3$ epitope borne on the $y_1$NANP antibody assumes a three-dimensional configuration that in immunological terms more closely mimics that of the active CS protein.

To determine whether the recombinant $y_1$NANP antibody could be used to induce anti-NANP antibodies, in vivo experiments were performed in rabbits. Two rabbits were immunized with the engineered $y_1$NANP antibody, and two controls receive the WT Ig. As indicated in Table I, infra., as early as 30 days after the first immunization, both rabbits immunized with the $y_1$NANP antibody produced anti-NANP antibodies detectable by ELISA and RIA. After booster immunizations, the titer rose in both rabbits; the maximal titer was 1/3200 on day 70. Importantly, this antiserum was positive when tested by indirect immunofluorescence on *P. falciparum* sporozoite showing that the epitope expressed by the $y_1$NANP Ig is indeed mimicking the native antigen. Sera from control rabbits immunized with the WT Ig did not react with the (NANP)$_3$ peptide immobilized on microtiter wells nor with the parasite. Rabbits of both groups produced an anti-human response as determined by agglutination of red cells coated with human gamma globulin. Rabbits' antisera were tested by direct immunofluorescence on *P. falciparum* (strain Indochina III) dried onto glass slides in the presence of 10% fetal bovine serum.

The observation that the $V_H$ region of an antibody molecule can be engineered to express 15 amino acid residues containing an epitope of an unrelated molecule shows that the $V_H/C_H$ polypeptide chain containing the foreign epitope is properly assembled with the endogenous L chain to form a ($H_2L_2$) tetramer, so it appears that the insertion of this epitope in the CDR3 was tolerated and did not affect the overall Ig framework folding. Based upon the present research, as long as the recombinant epitope is stereochemically compatible with contiguous CDR residues, it can be inserted or substituted for a CDR and can be expected to be exposed at the surface of the molecule, although it cannot be ruled out that the results reported here may be due to the nature of the epitope itself. In the construct described here, the (NANP)$_3$ sequence is flanked on both sides by the amino acids Val and Pro. Possibly, this helps stabilize the inserted epitope by anchoring it at each end. The large ramification at the Cβ atom and the C$_\gamma$-methyl group of the Val residue may hinder the main chain by decreasing its flexibility; the side chain of Pro by curling back to the main chain seizes it, leading to the formation of an almost rigid side chain.

Studias in vitro using the binding site of a NANP-specific monoclonal antibody as a probe for the protein-surface interaction and in vivo demonstrating that rabbits immunized with the engineered Ig molecule produce anti-NANP antibodies that react with the plasmodium antigen show that the (NANP)$_3$ epitope expressed by the engineered Ig is both antigenic and immunogenic. In other terms, neither the molecular environment nor the globular folding of Ig modified the immunologic structure of the (NANP)$_3$ epitope. From a biological standpoint, the (NANP)$_3$ epitope engineered into an Ig molecule can be viewed as an idiotope a la carte built into the CDR3 of a host $V_H$ domain. Based on what is known of the immunogenicity of idiotypes and the predictable events that follow induction of immunity via the idiotype network [Jerne *Ann. Immunol.* (Paris) 125, 373 (1974); Cozenave et al., *PNAS* 74, 5122 (1977); Urbain et al., *PNAS* 74, 5126 (1977); Bona et al., *J. Exp. Med* 153, 951 (1981)], these results imply that an immune response of predetermined epitope specificity can be dictated in molecular terms and predicted in vitro. This strategy can be exploited to render a B-cell epitope T-independent, proving its utility not only for analyses of the structure and function of epitopes and Igs but also for the development of new antibody vaccines, for example, as an alternative to peptide based vaccines. Preparation of vaccines may be accomplished using extant methology, already developed for immunoglobulins as such.

TABLE I

Induction of Anti-NANP Antibodies in Rabbits Immunized with the Engineered y$_1$NANP Antibody[a]

| Rabbit No. | Immunogen | Days After Immunization | | | | |
|---|---|---|---|---|---|---|
| | | 0 | 30* | 40 | 60* | 70 |
| 44 | WT | 0 | ND | 0 | 0 | 0 |
| 45 | WT | 0 | ND | 0 | 0 | 0 |
| 49 | y$_1$NANP | 0 | 1/100 | 1/400 | 1/400 | 1/3200 |
| 50 | y$_1$NANP | 0 | 0 | 1/400 | 1/200 | 1/1600 |

[a]Adult white rabbits were immunized subcutaneously in several points of the back with 50 μg of recombinant y$_1$NANP or the WT antibody emulsified in complete Freund's adjuvant (CFA). Booster injections of 50 μg of the same immunogen in incomplete Freund's adjuvant were given at monthly intervals (denoted by an asterisk). Sera were collected on the days indicate and tested for reactivity with the synthetic (NANP)$_3$ peptide by solid-phase ELISA and RIA. Briefly, serial twofold dilutions of individual sera in phosphate-buffered saline, pH 7.3, containing 1% bovine serum albumin and 1% Tween 20 ere incubated overnight at +4° C. on microtiter plates coated with the (NANP)$_3$ peptide at 5 μg/ml in 0.9% NaCl. After the incubation, the plates were washed and incubated with either a horseradish peroxidase conjugated goat anti-rabbit Ig, or $^{125}$I-labelled Protein A (Amersham) for one hour at room temperature. Next, the plates were washed and the bound antibodies determined by using a Bio-Rad (Richmond, Calif.) ELISA reader or a gamma counter. The binding of the preimmune sera was considered the reference background value. The titer was determined from the mean binding of triplicate samples after subtracting the background binding values and is expressed as the reciprocal serum dilution.

The foregoing description details specific methods that can be employed to practice the present invention. Having detailed specific methods initially used to identify, isolate, characterize, prepare and use the immunoglobulins hereof, and a further disclosure as to specific model entities, the art skilled will well enough know how to devise alternative reliable methods for arriving at the same information and for extending this information to other intraspecies and interspecies related immunoglobulins. Thus, however detailed the foregoing may appear in text, it should not be construed as limiting the overall scope hereof; rather, the ambit of the present invention is to be governed only by the lawful construction of the appended claims.

We claim:

1. An immunoglobulin molecule containing a tetrapeptide Asn-Ala-Asn-Pro epitope within the third complementarity-determining region in the N-terminus variable domain thereof, said immunoglobulin molecule having the effector function conferred by the constant region of the immunoglobulin, wherein said tetrapeptide is capable of eliciting an antibody response.

2. The immunoglobulin molecule according to claim 1 wherein the variable domain is composed of mouse sequences and the constant region is composed of human sequences.

3. The immunoglobulin molecule according to claim 1 wherein said tetrapeptide is present in treble form.

* * * * *